(12) United States Patent
Abels et al.

(10) Patent No.: US 6,964,565 B2
(45) Date of Patent: Nov. 15, 2005

(54) TWO-PART ORTHODONTIC BRACKET

(76) Inventors: Norbert Abels, Talstrass7, 66424 Homburg (DE); Claus H. Backes, St. Wendler Strasse 45, 66113 Saarbrüken (DE)

( * ) Notice: Subject to any disclaimer, the term of this patent is extended or adjusted under 35 U.S.C. 154(b) by 70 days.

(21) Appl. No.: 10/782,487

(22) Filed: Feb. 19, 2004

(65) Prior Publication Data

US 2005/0186525 A1 Aug. 25, 2005

(51) Int. Cl.⁷ ................................................. A61C 3/00
(52) U.S. Cl. ........................................... 433/10; 433/11
(58) Field of Search ............................. 433/10, 11, 12, 433/13, 14, 16, 17

(56) References Cited

U.S. PATENT DOCUMENTS

| | | |
|---|---|---|
| 2,011,575 A | 8/1935 | Ford |
| 3,128,552 A | 4/1964 | Broussard |
| 3,218,713 A | 11/1965 | Wallshein |
| 3,724,074 A | 4/1973 | Wallshein |
| 3,748,740 A | 7/1973 | Wildman |
| 3,854,207 A | 12/1974 | Wildman |
| 4,077,126 A | 3/1978 | Pletcher |
| 4,103,423 A | 8/1978 | Kessel |
| 4,144,642 A | 3/1979 | Wallshein |
| 4,171,568 A | 10/1979 | Förster |
| 4,180,912 A | 1/1980 | Kesling |
| 4,279,593 A | 7/1981 | Röhlcke |
| 4,355,975 A | 10/1982 | Fujita |
| 4,371,337 A | 2/1983 | Pletcher |
| 4,419,078 A | 12/1983 | Pletcher |
| 4,492,573 A | 1/1985 | Hanson |
| 4,527,975 A | 7/1985 | Ghafari et al. |
| 4,559,012 A | 12/1985 | Pletcher |
| 4,559,013 A | 12/1985 | Amstutz et al. |
| 4,597,739 A | 7/1986 | Rosenberg |
| 4,614,497 A | 9/1986 | Kurz |
| 4,634,662 A | 1/1987 | Rosenberg |
| 4,655,708 A | 4/1987 | Fujita |
| 4,687,441 A | 8/1987 | Klepacki |
| 4,698,017 A | 10/1987 | Hanson |
| 4,712,999 A | 12/1987 | Rosenberg |
| 4,786,252 A | 11/1988 | Fujita |
| 4,846,681 A | 7/1989 | Mourany et al. |
| 4,850,865 A | 7/1989 | Napolitano |
| 4,859,179 A | 8/1989 | Kesling |

(Continued)

FOREIGN PATENT DOCUMENTS

DE   1 184 451   12/1964

(Continued)

OTHER PUBLICATIONS

Konstruieren mit unststoffen, Gunter Erhard, Carl Hanser Verlag Müchen Wien, pp. 314-329, 1999.

Primary Examiner—Cary E. O'Connor
(74) Attorney, Agent, or Firm—Workman Nydegger (57) ABSTRACT

A two-part orthodontic bracket comprises a base and a holding device produced separately therefrom, with the base and the holding device being connected to one another via a joint having a pivot axis. The holding device can be selectively moved about the pivot axis between open and closed positions relative to the base and slot. When in an open position, the holding device can also be tilted about at least one tilt axis lateral or perpendicular to the pivot axis in order to provide better clearance in the case of tooth crowding. A guide system may also be provided that reduces the ability of the holding device to tilt as it is moved toward the closed position.

21 Claims, 8 Drawing Sheets

U.S. PATENT DOCUMENTS

| | | |
|---|---|---|
| 4,913,654 A | 4/1990 | Morgan et al. |
| 5,037,296 A | 8/1991 | Karwoski |
| 5,062,794 A | 11/1991 | Miura |
| 5,078,596 A | 1/1992 | Carberry et al. |
| 5,094,614 A | 3/1992 | Wildman |
| 5,125,832 A | 6/1992 | Kesling |
| 5,160,260 A | 11/1992 | Chang |
| 5,161,969 A | 11/1992 | Pospisil |
| 5,174,754 A | 12/1992 | Meritt |
| 5,224,858 A | 7/1993 | Hanson |
| 5,269,681 A | 12/1993 | Degnan |
| 5,275,557 A | 1/1994 | Damon |
| 5,322,435 A | 6/1994 | Pletcher |
| 5,344,315 A | 9/1994 | Hanson |
| 5,380,197 A | 1/1995 | Hanson |
| 5,429,499 A | 7/1995 | Sernetz |
| 5,456,599 A | 10/1995 | Hanson |
| 5,470,228 A | 11/1995 | Franseen et al. |
| 5,474,445 A | 12/1995 | Voudouris |
| 5,474,446 A | 12/1995 | Wildman et al. |
| 5,556,276 A | 9/1996 | Roman et al. |
| 5,562,444 A | 10/1996 | Heiser et al. |
| 5,586,882 A | 12/1996 | Hanson |
| 5,630,715 A | 5/1997 | Voudouris |
| 5,630,716 A | 5/1997 | Hanson |
| 5,685,711 A | 11/1997 | Hanson |
| 5,711,666 A | 1/1998 | Hanson |
| 5,738,513 A | 4/1998 | Hermann |
| 5,857,849 A | 1/1999 | Kurz |
| 5,863,199 A | 1/1999 | Wildman |
| 5,885,074 A | 3/1999 | Hanson |
| 5,906,486 A | 5/1999 | Hanson |
| 5,913,680 A | 6/1999 | Voudouris |
| 5,964,589 A | 10/1999 | Musich |
| 6,017,118 A | 1/2000 | Gasvoda et al. |
| 6,042,373 A | 3/2000 | Hermann |
| 6,042,374 A | 3/2000 | Farzin-Nia |
| 6,071,119 A | 6/2000 | Christoff et al. |
| 6,168,429 B1 | 1/2001 | Brown |

FOREIGN PATENT DOCUMENTS

| | | |
|---|---|---|
| DE | 23 57 573 | 5/1975 |
| DE | 91 12 872.2 | 3/1992 |
| DE | 296 08 349 U1 | 7/1996 |
| EP | 0 714 639 A2 | 5/1996 |
| EP | 0 714 639 A3 | 5/1996 |
| WO | WO 94/00072 | 6/1994 |
| WO | WO 00/33760 | 6/2000 |
| WO | WO 00/76419 | 12/2000 |

TWO-PART ORTHODONTIC BRACKET

CROSS-REFERENCE TO RELATED APPLICATIONS

Not applicable.

BACKGROUND OF THE INVENTION

1. The Field of the Invention

The present invention relates to a two-part orthodontic bracket comprising a base and a holding device produced separately therefrom, with the base and the holding device being fastened to one another via a connection device. In use, the holding device covers at least one slot for a wire and is movable by a closing movement from an open position into a closed position in which the holding device latches on the base.

2. Relevant Technology

A two-part orthodontic bracket having a base, an arch wire slot and a holding device is disclosed in WO 00/33760. However, when a bracket of this design is attached to a tooth surface of a patient whose teeth have strong crowding, such crowding can inhibit or prevent the holding devices of one or more brackets from being opened widely enough to easily place or remove an arch wire from the arch wire slot.

One-piece orthodontic brackets are known which have a base, an arch wire slot, and a holding device, with the base and the holding device being interconnected via a film hinge. In such brackets, the holding device can be tilted about an axis perpendicular to the pivot axis due to the flexibility of the film hinge. The inclusion of the film hinge limits the types of materials that can be used to make such one-piece brackets, particularly the film hinge itself, which must be flexible enough to allow opening and closing of the holding device.

In view of this, there is a need for improved two-part brackets in which the holding device has increased range of motion, or degrees of freedom, relative to the base to address problems associated with tooth crowding.

SUMMARY OF THE INVENTION

The present invention generally relates to a two-part orthodontic bracket that includes a base and a holding device that are interconnected by a connection device or joint. The base includes at least one slot for a wire. The holding device is designed to move between an open non-ligating position and a closed ligating position relative to the slot.

The connection device or joint is configured so as to permit the holding device to have multiple degrees of freedom of movement relative to the base while in the open position. In one embodiment, a guide system is provided that reduces the degrees of freedom of movement as the holding device is moved toward the closed position.

In accordance with the invention, the joint which interconnects the base and the holding device of the two-part orthodontic bracket is designed so that the holding device is movable about a pivot axis when the holding device is initially opened. When in the open position, the holding device is not only movable about the pivot axis, but it is also freely movable about one or more tilt axes that are lateral or perpendicular to the pivot axis. The ability of the holding device to tilt about one or more tilt axes when partially or completely open allows for sufficient opening of the holding device and exposure of the slot in the case of even high tooth crowding. In this way, the holding device can be manipulated by moving it in an appropriate direction past an adjacent tooth.

In one embodiment, the free movability of the holding device relative to the base may be limited or reduced as the holding device is moved toward the closed position. In one embodiment, the degrees of freedom of the holding device are reduced during closing of the holding device by a guide system. When the holding device is latched to the base in the closed state, the wire is held in the slot and the holding device is simultaneously fixed substantially immovably to the base.

In accordance with a first embodiment, a guide system for limiting or reducing the degrees of freedom of the holding device relative to the base can be provided at, or as part of, the connection device. It is also possible for the guide system to form part of the base and/or holding device.

In accordance with a further embodiment, the guide system can be configured such that the reduction of free movability of the holding device is initiated independently of latching. In other words, the guide system can be designed so that the free movability of the holding device is already reduced before the holding device is actually closed and/or latched to the base.

In one embodiment, the guide system can be configured so that the base and holding device can only be latched in a precisely fixed or pre-defined spatial relationship to one another, i.e., the guide system helps define the position of the holding device relative to the base before and also after latching.

According to one embodiment, the at least partially open holding device is preferably tiltable about a tilt axis that is different from the pivot axis so as to be moveable about a tilt angle in a range of about 0.5° to about 10°, preferably in a range of about 1° to about 8°. A tilt angle within these ranges is sufficient in many cases to move the at least partially open holding device past an adjacent tooth, thus overcoming potential problems associated with tooth crowding.

With a horizontally arranged base, a tilt axis can extend substantially horizontally so that a holding device in a vertical position is tiltable in a vertical plane about the horizontal tilt axis. Alternatively, a tilt axis can extend substantially vertically with a horizontally arranged base so that a holding device in the vertical position is tiltable about the vertical axis. In one embodiment, the bracket can have horizontal and vertical tilt axes in order for a holding device in a vertical position to be selectively tiltable about one or both of the horizontal and vertical tilt axes.

In one embodiment, the joint can be made such that the at least partially open holding device is movable about any three desired axes perpendicular to one another. This configuration more easily permits the holding device to be manipulated so as to be movable past an adjacent tooth in order to permit sufficient opening of the holding device. This helps facilitate insertion or removal of an arch wire from the slot.

In accordance with an additional embodiment of the invention, the joint can form a movable bearing for the at least partially open holding device in order to ensure a sufficient or desired amount of tilting of the holding device relative to the base. Of course the holding device is typically not tilted when latched to the base.

In accordance with a further embodiment of the invention, the joint may comprise at least one spigot that is received at least partially within a link guide, with the spigot and the link guide being be arranged either on the base or on the holding device. In one aspect the link guide serves to permit pivoting of the holding device about the pivot axis so that it can be opened and closed relative to the base. In another aspect the link guide permits tilting of the holding device relative to the base about one or more tilt axes that are lateral or perpendicular to the pivot axis when the holding device is in an open position.

To maintain the holding device on the base in a latched or closed state substantially without clearance or movement, while also permitting tilting of the holding device when in an at least partially open position relative to the base, the link guide may have a first peripheral section having a curvature that corresponds to the curvature of the spigot and a second peripheral section having a curvature that is greater than the curvature of the first peripheral section. It is ensured in this embodiment that the spigot has close contact in the region of the first peripheral section of the link guide when the holding device is in a completely closed or latched state, while also permitting tilting of the spigot inside the link guide when the holding device is at least partially open.

In accordance with a further embodiment, the joint may comprise two spigots which are each received in a respective link guide, with at least one link guide not surrounding the associated spigot along its total periphery. In this embodiment, a passage opening is provided in the at least one link guide. This facilitates assembly of the holding device and base by permitting insertion of a connection web interconnecting the spigots through the passage opening during assembly of the two-part bracket.

In accordance with a further embodiment of the invention, a snap connection can be provided which securely holds the holding device to the base while still permitting free movement of the holding device about the various axes described herein. In one embodiment, the passage opening is ramped so as to cause the associated link guide to temporarily spread open during assembly, more particularly, as the connection web is inserted therethrough. Upon fully inserting the connection web into a space between the two link guides, the passage opening snaps back so as to lock the holding device to the base while also permitting free movement of the holding device about the various axes.

The bracket in accordance with the invention is preferably made of a bite-proof material, for example of metal, rigid plastic or ceramic. In one embodiment of the invention, the holding device comprises a cover.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings, in which.

DETAILED DESCRIPTION OF THE PREFERRED EMBODIMENTS

The invention generally relates to a two-part orthodontic bracket including a base and a holding device that are interconnected in a manner that allows the holding device to move or tilt about a plurality of axes while in the open position. In this way, the holding device has multiple degrees of freedom so that it can be moved past an adjacent tooth when moved to the open position so as to expose a slot for an arch wire. Following are exemplary embodiments of two-part orthodontic brackets according to the invention.

Figures 1, 2, 3:
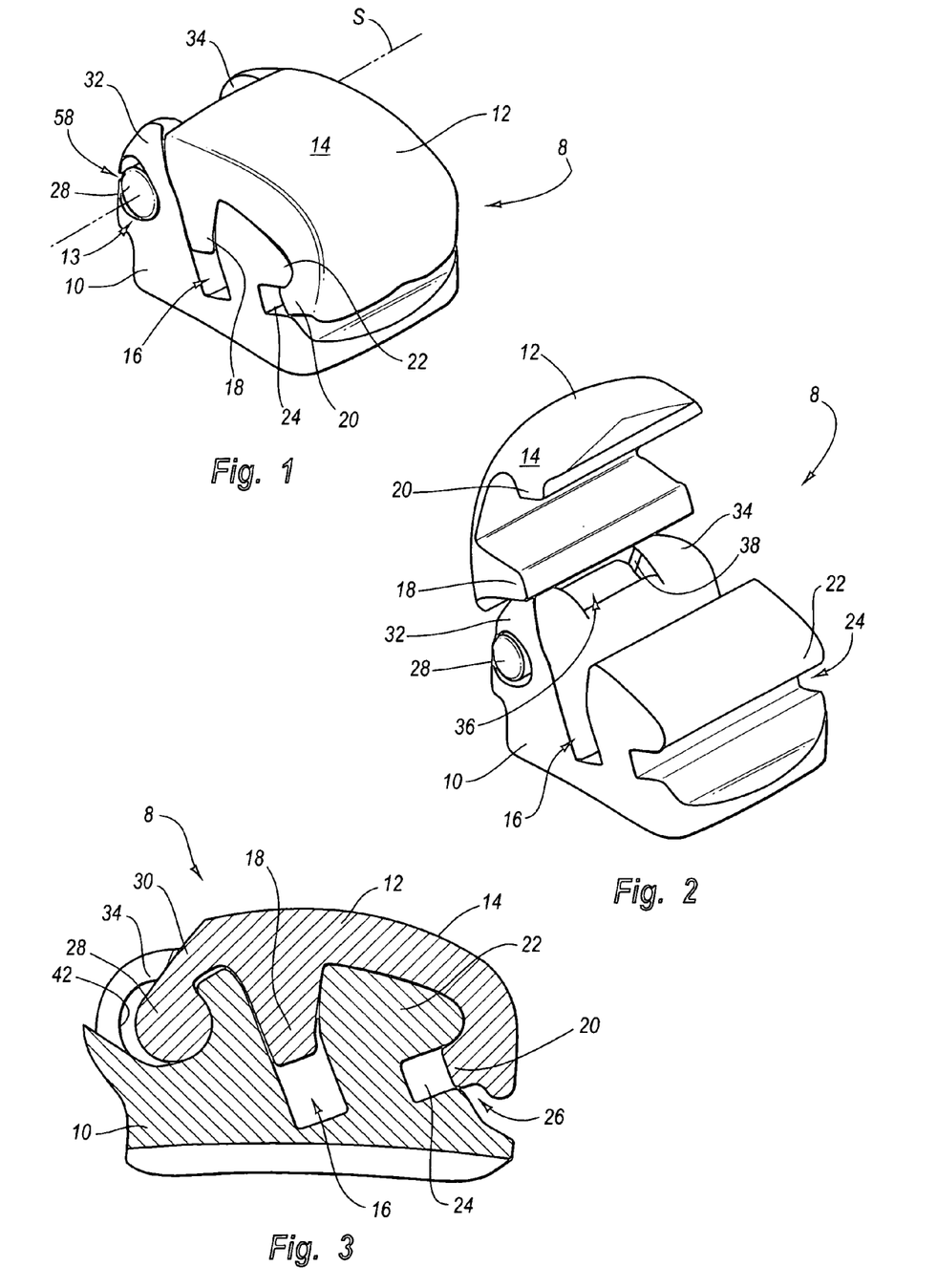
FIG. 1 is a perspective view of an exemplary two-part orthodontic bracket according to the invention with the holding device in a closed and latched position.
FIG. 2 is a perspective view showing the bracket of FIG. 1 but with an open holding device.
FIG. 3 is a longitudinal cross-sectional view of the closed bracket of FIG. 1.

FIG. 1 shows a two-part orthodontic bracket 8 which consists of a base 10 and a holding device 12 which can be produced separately therefrom. The base 10 and holding device 12 are pivotally connected to each other via a joint 13 which has a horizontal pivot axis S about which the holding device 12 can be pivoted from its completely closed and latched position shown in FIG. 1 into an open position (e.g., as shown in FIG. 2). The joint 13 is an example of a connection device according to the invention.

In the embodiment shown, the holding device 12 comprises a cover having a smooth, curved outer surface 14. It will be appreciated that the holding device 12 can have other shapes as desired to yield an orthodontic bracket having a desired configuration and functionality.

As further illustrated in FIG. 1, the holding device 12, while in a completely closed or latched state relative to the base 10, covers or occludes a slot 16 designed to receive therein an arch wire (not shown). The holding device 12 is advantageously provided with an extension 18 designed to bear against and hold an arch wire in slot 16 when the holding device 12 is closed or latched relative to the base 10, as better seen in FIG. 3.

In accordance with the invention, the joint 13 is formed between the holding device 12 and the base 10 in a manner so as to permit the holding device 12 to be tilted about at least one tilt axis that is lateral or perpendicular to the pivot axis S when the holding device 12 is at least partially open relative to the base 10. In this way the holding device 12, while in an at least partially open position, is movable relative to the base 10 about at least two axes that are lateral or perpendicular to each other. A guide (which is explained in more detail below) can be provided (e.g., as part of the joint or connection device) that progressively limits the ability of the holding device 12 to tilt relative to the base 10 as the holding device 12 is moved toward the closed or latched position.

FIG. 1 further illustrates an orthodontic bracket 8 in which the holding device or cover 12 and the base 10 form, in the closed or latched state, a substantially uniformly curved surface 14 having no sharp or jagged corners or edges that might irritate a user of the bracket 8. This prevents or reduces potential injury and discomfort to the patient, as well as the tendency of food or other foreign substances to catch or adhere to the bracket 8.

The holding device 12 can be latched or locked to the base 10 in order to maintain the holding device 12 in a closed or latched state by means of a latch projection 20 provided at an end of the holding device 12 distal to the joint 13. The latch projection 20 generally extends toward the base 10 and is configured so as to snap over a latch bump 22 provided at the base 10 in order to mechanically latch the holding device 12 to the base 10.

As shown in FIGS. 1–4, an auxiliary slot 24 may be provided in the base 10 in the region of the latch projection 24, which, in one embodiment, extends parallel to the main slot 16 and is likewise covered when the holding device 12 is completely closed or latched so as to fix or ligate an arch wire that may optionally be provided in the auxiliary slot 24.

As best seen in FIG. 3, an engagement gap 26 may advantageously be provided at the anterior side of the bracket 8 between the base 10 and the holding device 12 when the holding device 12 is the completely closed or latched position. A dental tool (not shown) can be inserted into the engagement gap 26 in order to engage and unlatch the holding device 12 from the base 10.

Figure 4A:
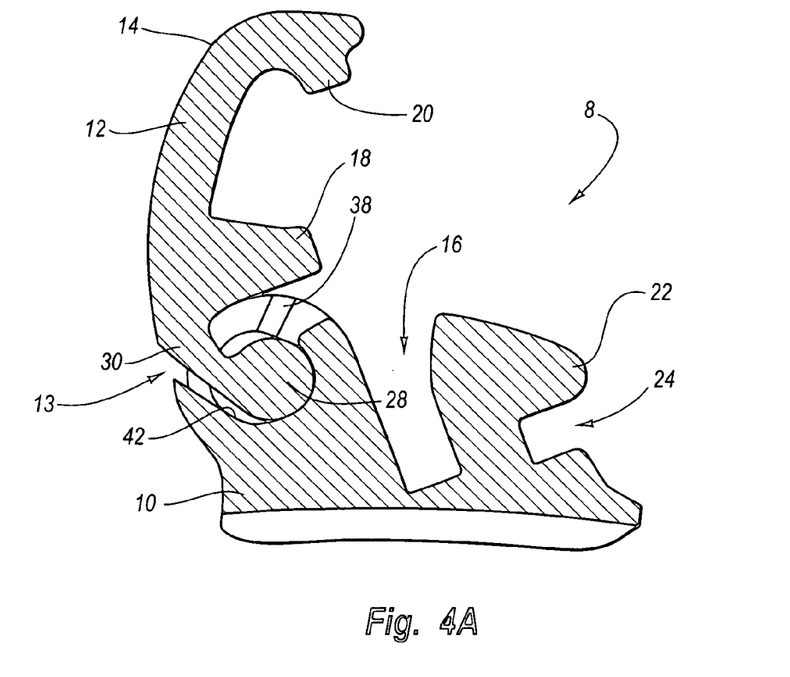
FIGS. 4A–4C are longitudinal cross-sectional views of the open bracket of FIG. 3, but with different tilting arrangements of the holding device in each of FIGS. 4B and 4C.
Figure 4B:
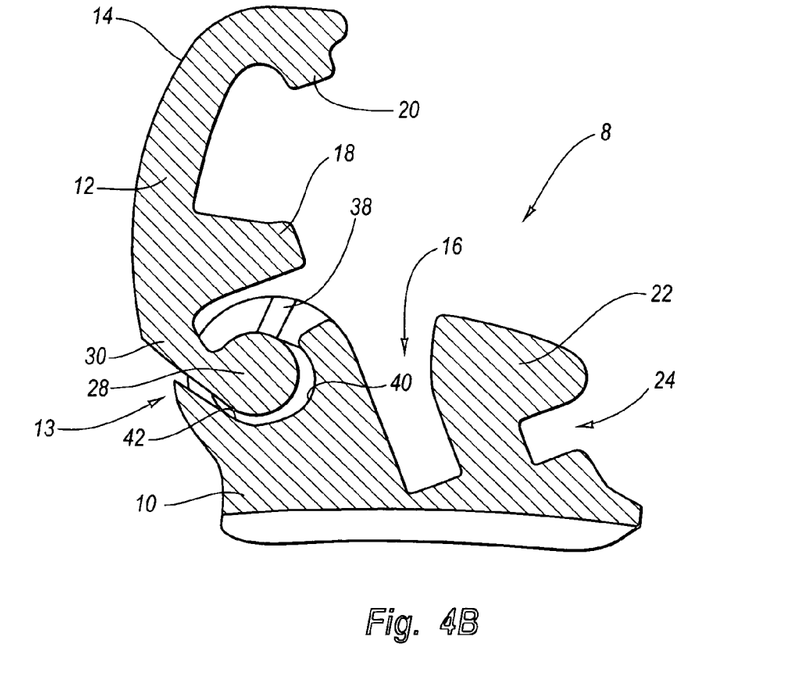
Figure 4C:
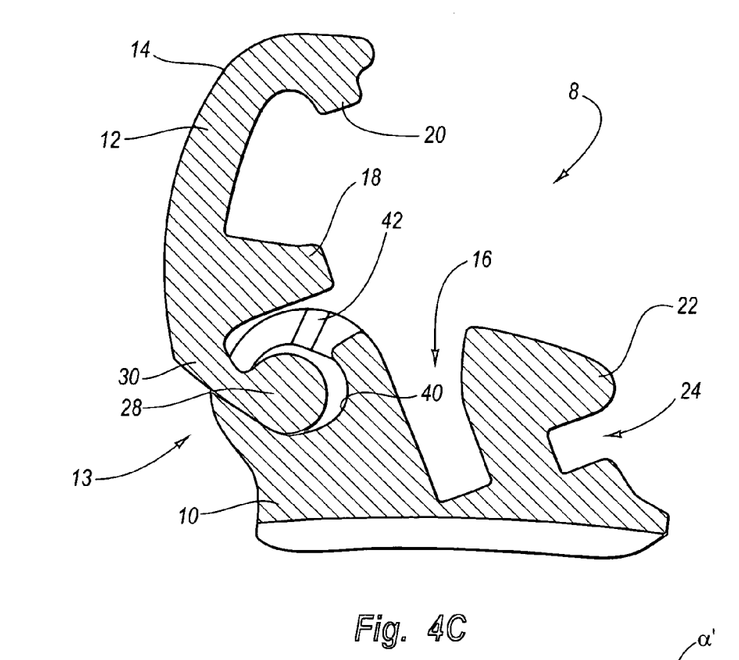

As best seen in FIGS. 3 and 4, the orthodontic bracket 8 further includes, in the embodiment shown, a pair of spigots 28 which are connected to the holding device 12 by means of a connection web 30. In one embodiment, the spigots 28 have a cylindrical cross-section. The spigots 28 are each received in a respective link guide 32 and 34 connected to a base 10. The spigots 28 and link guides 32 and 34 together comprise at least a portion of joint 13. The interaction between the spigots 28 and link guides 32 and 34 allow the holding device 12 to be rotated about the pivot access S between the open and closed positions.

As best seen in FIG. 2, the link guides 32 and 34 are in a spaced-apart relationship and include opposing inner surfaces that together define a guide recess 36. The inner surfaces of the link guides 32 and 34 also include chamfers 38. In use, the connection web 30 of the holding device 12 can be inserted into the guide recess 36 while closing the holding device 12 relative to the base 10. The guide recess 36 and the connection web 30 are configured so that, when the holding device 12 is completely closed, lateral displacement of the holding device 12 relative to the base 10 along the axis S is prevented or at least minimized within a desired range. The chamfers 38 cause or represent a narrowing of the guide recess 36 so as to thereby channel the connection web 30 from a region of greater width of the guide recess 36 to a region of narrower width as the holding device 12 is moved toward the closed position. This action is more clearly illustrated in FIGS. 7A–7C, which are discussed more fully below.

As illustrated more particularly in FIGS. 4A–4C, the joint 13 between the base 10 and the holding device 12 forms a movable bearing for the holding device 12 when at least partially open relative to the base 10. The inner peripheral surface of the link guides 32 and 34 has a first peripheral section 40 and a second peripheral section 42. The curvature of the first peripheral section 40 corresponds to the cylindrical curvature of the outer periphery of the spigots 28, and the curvature of the second peripheral section 42 is greater than the curvature of the first peripheral section 40. This curvature differential causes the spigots 28 to more tightly contact the first peripheral section 40 when the holding device 12 is in a completely closed position (FIGS. 3 and 6E) and also when the holding device is in a slightly open position (FIG. 6D). Conversely, the spigots 32 and 34 more loosely contact the second peripheral section 42 when the holding device 12 is in an open position.

In one embodiment, the position of the holding device 12 relative to the base 10 shown in FIGS. 3 and 4A defines the pivot axis S. At the same time, however, it is possible when the holding device 12 is partially or completely open to move the spigots 28 within the link guides 32 and 34 so as to adopt other positions, such as those illustrated in FIGS. 4B, 4C, 5A and 5B, in which the peripheral surfaces of the spigots 28 do not contact the first peripheral section 40 of one or both link guides 32 and 34. The holding device 12 is therefore not limited to being pivoted about the pivot axis S only, but may also be tilted about different tilt axes different from the pivot axis S.

Figure 5A:
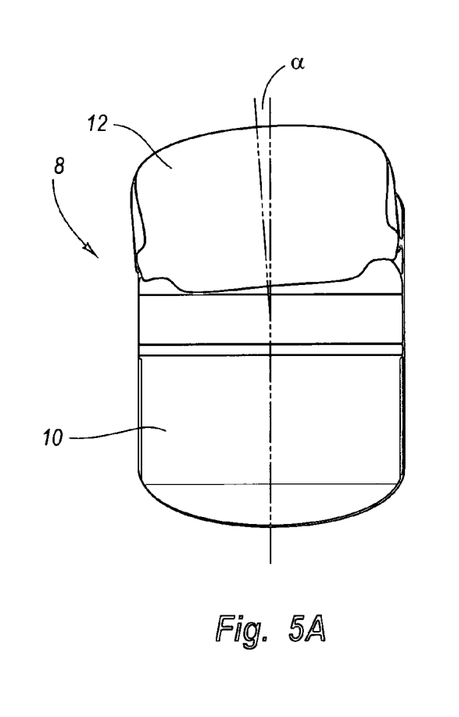
FIG. 5A is a plan view of the bracket of FIG. 2 showing a holding device that has been tilted about a vertical axis.

FIG. 5A shows a plan view of the bracket shown in FIG. 2, with the holding device 12, however, having been tilted about a vertical tilt axis such that (in the embodiment shown) a tilt angle α of approximately 5° results. In this position, the right hand spigot 28 in FIG. 5A, for example, would adopt a position inside the link guide 36 corresponding to FIG. 4B or 4C, whereas the left hand spigot 28 in FIG. 5A would adopt the position corresponding to FIG. 4A.

Figure 5B:
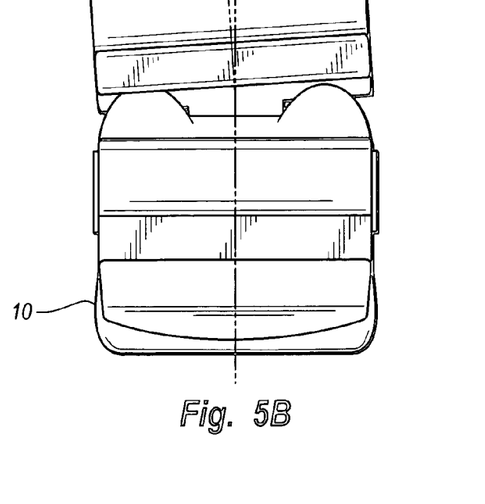
FIG. 5B is an elevation view of the bracket of FIG. 2 showing a holding device that has been tilted about a horizontal axis.

FIG. 5B shows an elevated view of the bracket shown in FIG. 2, with the holding device 12, however, having been tilted about a horizontal tilt axis such that (in the embodiment shown) a tilt angle α' of approximately 5° results. In this position, the right hand spigot 28 in FIG. 5B, for example, would adopt a position inside the link guide 36 corresponding to FIG. 4B, whereas the left hand spigot 28 in FIG. 5B would adopt a position corresponding to FIG. 4A or 4C.

It should be understood that the particular conformations or positions of the holding device 12 relative to the base shown in FIGS. 5A and 5B are merely illustrative and that various other conformations or positions are possible in order to maximize the ability to compensate for tooth crowding. Thus, it can be seen from FIGS. 4 and 5 that not only a tilting of the holding device 12 about a vertical tilt axis is possible, but also, within the limit pre-determined by the second peripheral section 42, any desired tilting of the holding device 12 relative to the base 10 and/or pivot axis S is possible.

Notwithstanding the ability of the holding device 12 to tilt in various ways when the holding device 12 is in a fully open position relative to the base 10, the degrees of freedom of such tilting may advantageously become progressively reduced as the holding device 12 is moved toward a closed position relative to the base 10. More particularly, as a result of the positioning and size of the link guides 32 and 34 relative to the positioning and size of a corresponding inner surface of the holding device 12, as well as the positioning and size of the connection web 30 relative to the guide recess 36, the degrees of freedom of the holding device 12 can be reduced as the holding device 12 is progressively moved toward the closed position. As the holding device 12 is closed it can be guided through the interaction of the link guides 32 and 34, inner surface of holding device 12, connection web 30 and guide recess 36 so as to adopt a precisely defined position relative to the base 10 prior to and after being completely latched to the base 10.

Figure 6A:
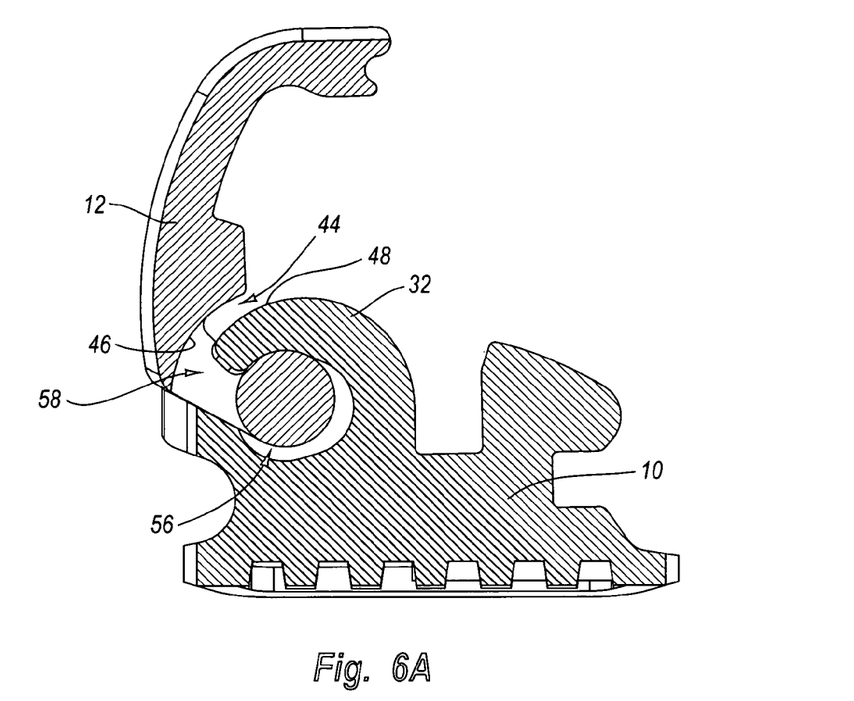
FIGS. 6A–6E are longitudinal cross-sectional views of an exemplary orthodontic bracket showing the spacing and interaction between corresponding surfaces of a link guide and a holding device as the holding device is progressively moved from the open position to the closed position.
Figure 6B:
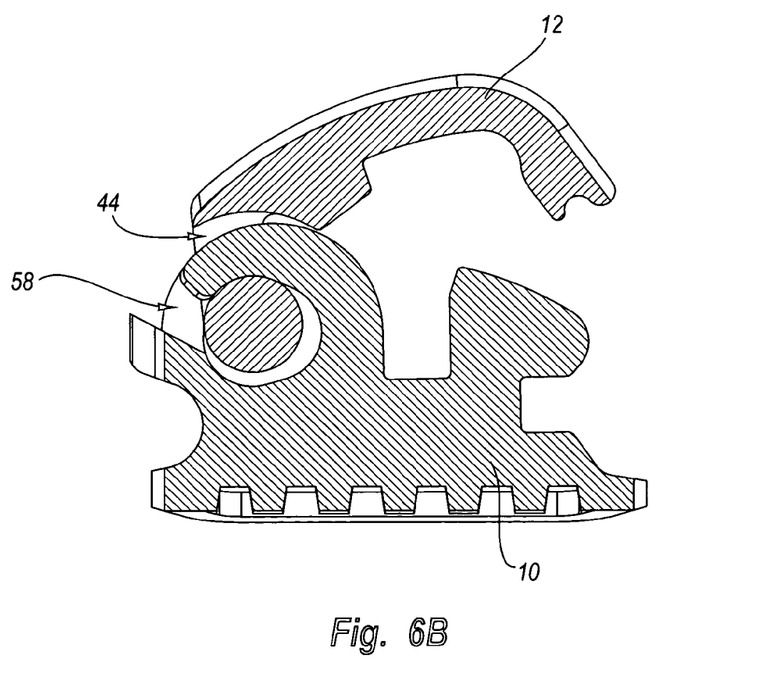

FIGS. 6A–6B illustrate the interaction between the link guides 32 and 34 and the corresponding surfaces of the holding device 12 in incrementally restricting the degrees of freedom or tiltability of the holding device 12 relative to the base 10 as the holding device is progressively moved towards the closed position according to one embodiment. As shown in FIG. 6A, a relatively large space 44 exists between an undersurface 46 of the holding device 12 and an outer surface 48 of link guide 32. The size of space 44 at least partially defines the amount of tiltability or degrees of freedom that exist between the holding device 12 and the base 10.

Figure 6C:
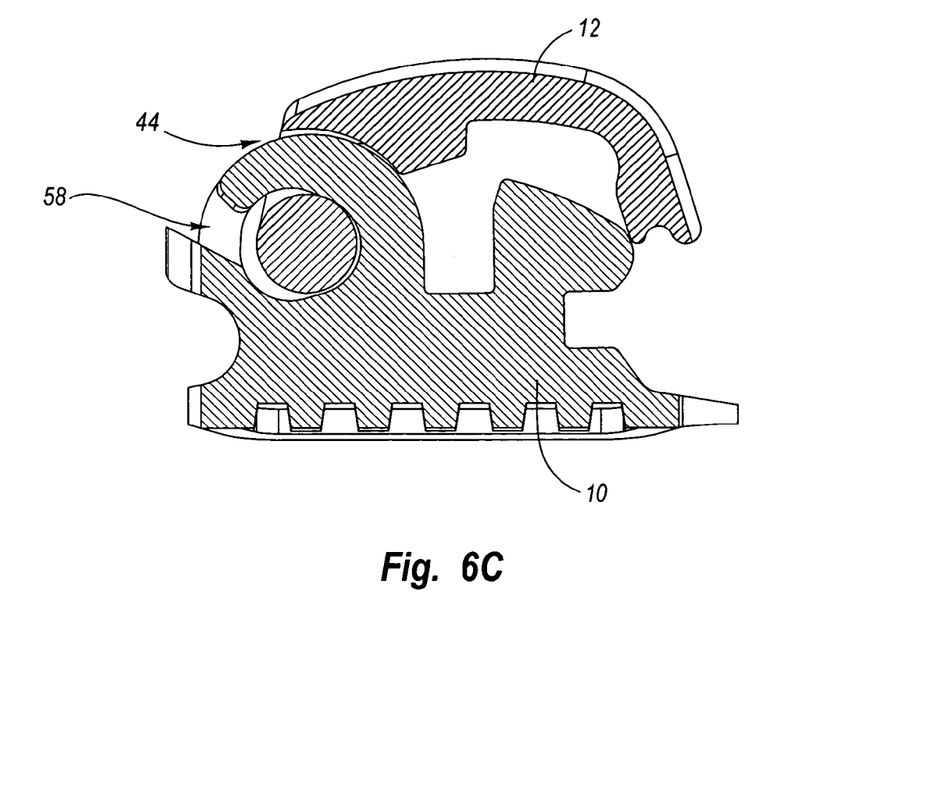
Figure 6D:
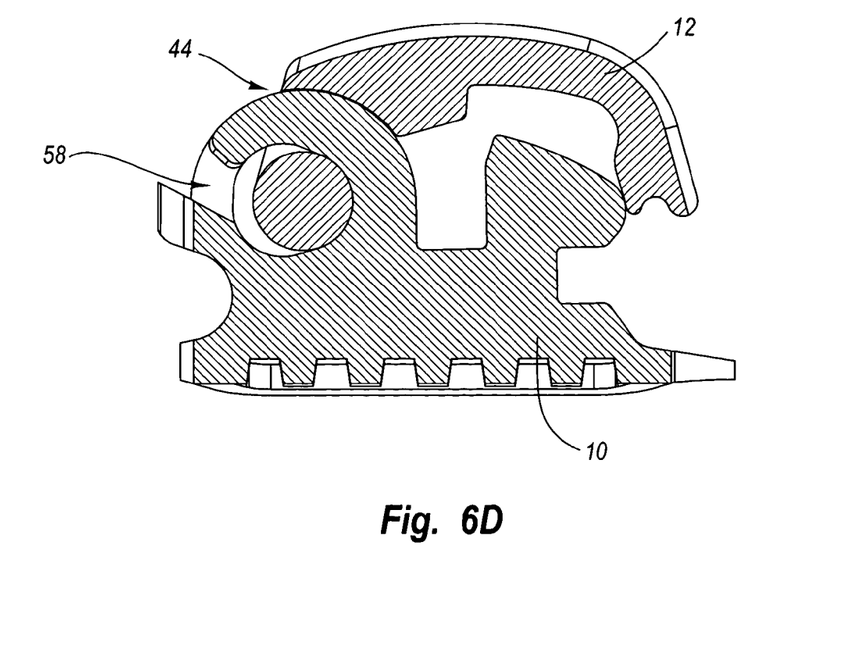
Figure 6E:
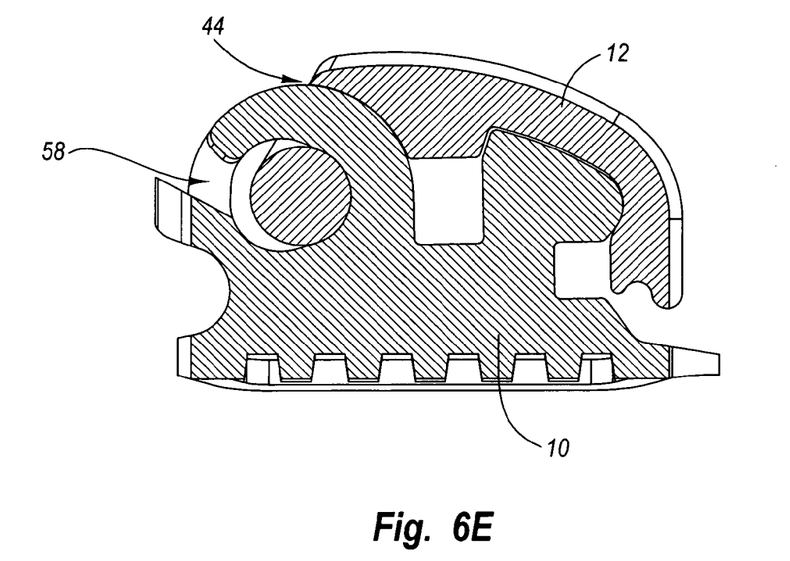

FIG. 6B shows a diminution in the size of space 44 as the holding device 12 is moved to an intermediate position between the fully opened and fully closed positions. The diminished size of space 44 limits the tiltability or degrees of freedom of the holding device 12 relative to the base 10. FIGS. 6C–6E show a further reduction in the size of space 44 until none remains when the holding device 12 is in the fully latched position (FIG. 6E) and in a position just prior to being latched (FIG. 6D).

Figure 7A:
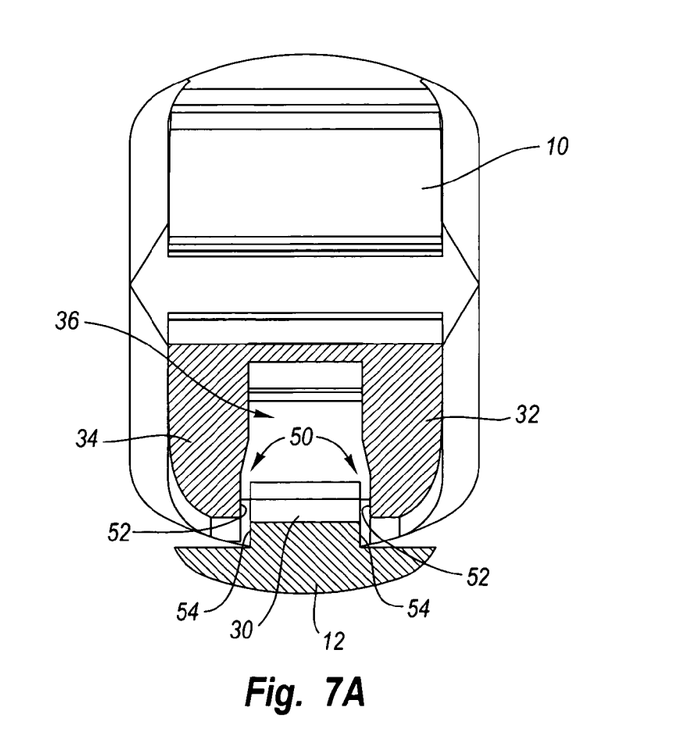
FIGS. 7A–7C are plan cross-sectional views of an exemplary orthodontic bracket showing the relationship between a connection web of a holding device and link guides as the holding device is progressively moved from the open to the closed position.
Figure 7B:
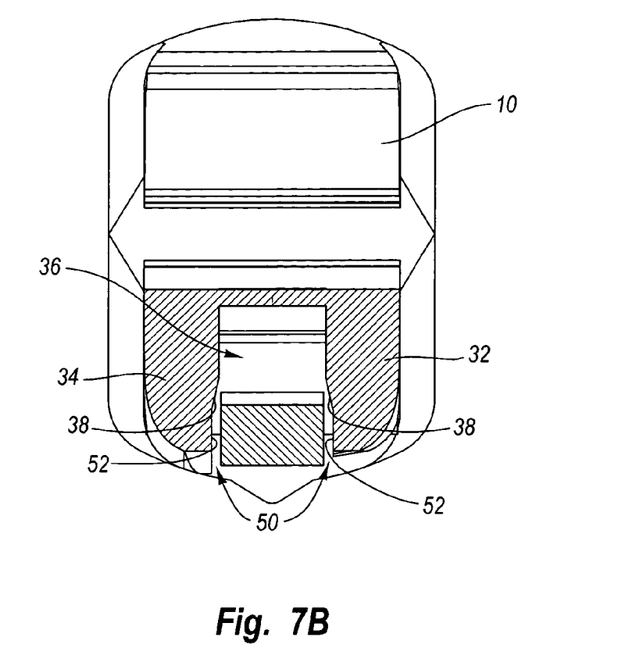
Figure 7C:
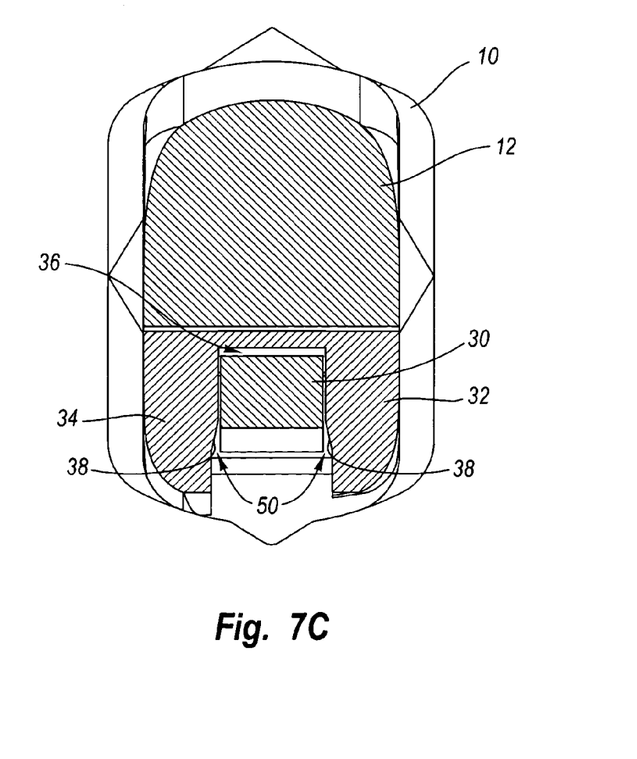

FIGS. 7A–7B illustrate the interaction between the inner surfaces of the link guides 32 and 34 defining the guide recess 36 and the connection web 30 of the holding device 12. As shown in FIG. 7A, when the holding device 12 is in the fully open position relative to the base 10, a pair of relatively large spaces 50 exist between inner surfaces 52 of link guides 32 and 34 and outer surfaces 54 of connection web 30.

FIG. 7B show a reduction in the size of spaces 50 as the holding device 12 is moved toward the closed position, particularly as the outer surfaces 54 of the connection web 30 pass by the chamfers 38 that define a narrowing of the space between the guide recess 36. As the size of spaces 50 diminishes, the ability of the holding device 12 to tilt relative to the base 32 and 34 and outer surfaces 54 of connection web 30 is correspondingly reduced. FIG. 7B show a reduction in the size of spaces 50 as the holding device 12 is moved toward the closed position, particularly as the outer surfaces 54 of the connection web 30 pass by the chamfers 38 that define a narrowing of the space within the guide recess 36. As the size of spaces 50 diminishes, the ability of the holding device 12 to tilt relative to the base 10 is correspondingly diminished.

Figure 8:
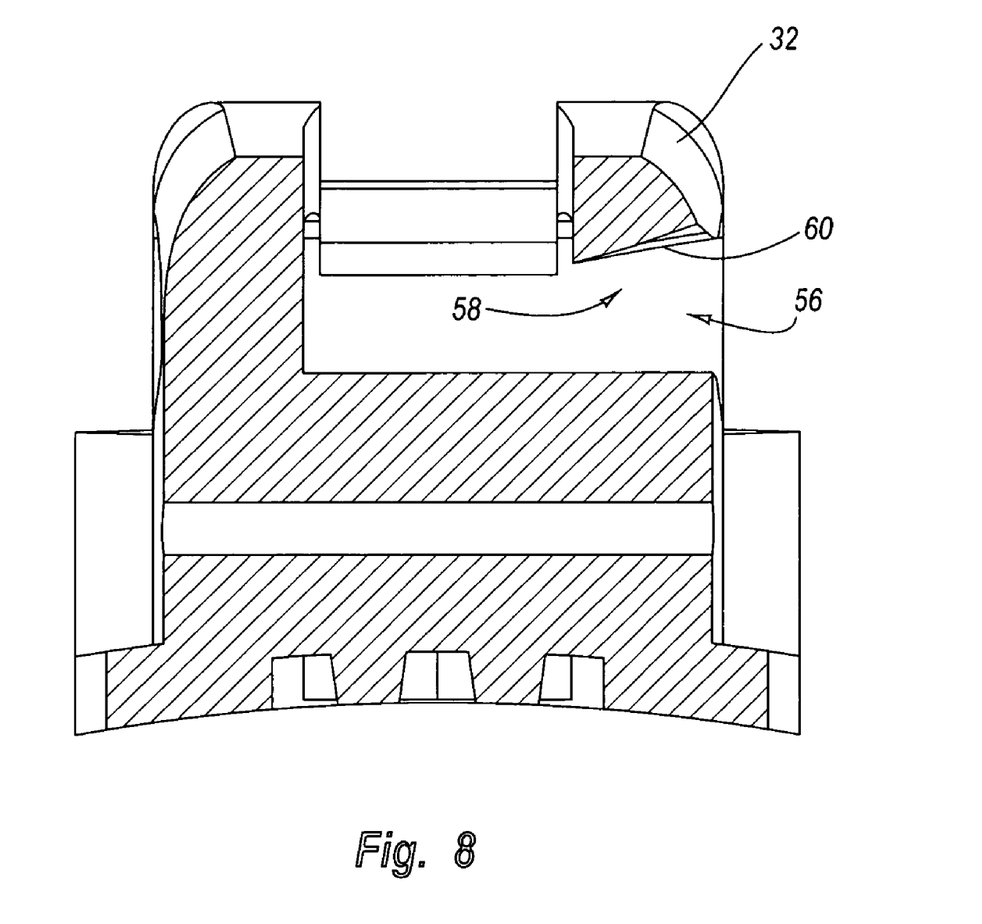
FIG. 8 is an elevation view of an exemplary bracket base showing a ramped passage opening in one of the two link guides for facilitating assembly of a holding device to the base.

As illustrated in FIG. 8, to facilitate assembly of the holding device 12 with the base 10, at least one of link guides 32 and 34 can be provided with a passage opening 56 which is dimensioned such that the spigots 28 can be pushed therethrough along the pivot axis S when the holding device 12 is in the completely open position (see FIGS. 2 and 4).

Link guide 32 further includes a secondary opening 58 having a ramped surface 60 that is inclined so as to cause the link guide 32 to be slightly stretched elastically so as to permit passage of the connection web 30 through the auxiliary passage 58. After the connection web 30 is fully inserted through the auxiliary passage 58, the link guide 32 snaps back to its original configuration, thereby forming a snap connection that captively retains the holding device 12 to the base 10. The auxiliary passage 58 is more clearly seen in FIGS. 6A through 6E.

It should be appreciated that the joint or of the aforesaid embodiment can also be realized in other manners. It is only necessary that the holding device 12 is freely movable relative to the base 10 about at least two different axes while in the open position, with a reduction of free movability preferably taking place as a result of guide system as the holding device 12 is moved toward the closed position.

The orthodontic brackets according to the invention may comprise any material. Preferably, the base and/or holding device may consist of a bite-proof material such as metal, ceramic or rigid plastic whose stiffness would not ordinarily permit torsion in the region of a joint.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A two-part orthodontic bracket, comprising:
   a base;
   at least one slot associated with the base configured to receive an arch wire;
   a holding device pivotally connected to the base in a manner so that the holding device is movable about a pivot axis between an open position and a closed position relative to the base and slot, and so that the holding device is tiltable relative to the base about at least one axis other than the pivot axis;
   a latch for selectively latching and unlatching the holding device and base; and
   a guide system that reduces tiltability of the holding device as the holding device is moved toward the closed position, and wherein the guide system causes a reduction in the tiltability of the holding device independently of latching the holding device to the base.

2. The two-part orthodontic bracket of claim 1, further comprising a connection device that pivotally connects the holding device to the base.

3. The two-part orthodontic bracket of claim 2, wherein the connection device comprises at least a portion of the guide system.

4. The two-part orthodontic bracket of claim 2, wherein the connection device comprises at least one spigot which is received in a corresponding link guide.

5. The two-part orthodontic bracket of claim 2, wherein the connection device comprises at least one spigot which is received in a corresponding link guide, with the curvature of a first peripheral section of the link guide corresponding to the curvature of the spigot and the curvature of a second peripheral section of the link guide being greater than that of the first peripheral section.

6. The two-part orthodontic bracket of claim 2, wherein the connection device comprises two spigots which are each received in a corresponding link guide, with at least one link guide not surrounding the associated spigot along its entire periphery.

7. The two-part orthodontic bracket of claim 2, wherein the connection device comprises at least one spigot which is received in a corresponding link guide which has a passage opening for a connection web between the holding device and the spigot.

8. The two-part orthodontic bracket of claim 7, wherein the connection device forms a snap connection that holds the holding device to the base.

9. The two-part orthodontic bracket of claim 1, wherein the base and the holding device are only latchable in a precisely fixed spatial relationship to one another due to the guide system.

10. The two-part orthodontic bracket of claim 1 wherein the holding device comprises a cover having a rounded outer surface.

11. The two-part orthodontic bracket of claim 1, wherein the holding device is tiltable about at least one tilt angle in a range of about 0.5° to about 10° when in the open position.

12. The two-part orthodontic bracket of claim 11, wherein the holding device is tiltable about at least one tilt angle in a range of about 1° to about 8° when in the open position.

13. The two-part orthodontic bracket of claim 11, wherein the at least one tilt axis extends substantially horizontally when the base is arranged horizontally.

14. The two-part orthodontic bracket of claim 11, wherein the at least one tilt axis extends substantially vertically when the base is arranged horizontally.

15. The two-part orthodontic bracket of claim 1, wherein the holding device is movable about three axes perpendicular to one another when in the open position.

16. The two-part orthodontic bracket of claim 1, wherein the guide system comprises a movable bearing for the at least partly open holding device.

17. The two-part orthodontic bracket of claim 1, wherein the bracket comprises at least one of a metal, ceramic or rigid plastic.

18. A two-part orthodontic bracket, comprising:
a base;
at least one slot associated with the base configured to receive an arch wire;
a holding device pivotally connected to the base in a manner so that the holding device is movable about a pivot axis between an open position and a closed position relative to the base and slot, and so that the holding device is tiltable relative to the base about at least one axis other than the pivot axis; and
a connection device that pivotally connects the holding device to the base and that comprises a guide system that reduces tiltability of the holding device as the holding device is moved toward the closed position.

19. A two-part orthodontic bracket, comprising:
a base;
at least one slot associated with the base configured to receive an arch wire;
a holding device pivotally connected to the base in a manner so that the holding device is moveable about a pivot axis between an open position and a closed position relative to the base and slot, so that the holding device is tiltable relative to the base about at least one axis other than the pivot axis; and
a connection device that pivotally connects the holding device to the base, the connection device comprising:
at least one spigot attached to an end of the holding device by a connection wire; and
at least one link guide attached to the base into which a portion of a corresponding spigot is received.

20. A two-part orthodontic bracket, comprising:
a base;
at least one slot associated with the base configured to receive an arch wire;
a holding device pivotally connected to the base in a manner so that the holding device is movable about a pivot axis between an open position and a closed position relative to the base and slot, and so that the holding device is tiltable relative to the base about at least one axis other than the pivot axis;
a connection device that pivotally connects the holding device to the base, and wherein the connection device comprises at least a portion of the guide system; and
a guide system that reduces tiltability of the holding device as the holding device is moved toward the closed position.

21. A two-part orthodontic bracket, comprising:
a base;
at least one slot associated with the base configured to receive an arch wire;
a holding device pivotally connected to the base in a manner so that the holding device is movable about a pivot axis between an open position and a closed position relative to the base and slot, and so that the holding device is tiltable relative to the base about at least one axis other than the pivot axis; and
a guide system that reduces tiltability of the holding device as the holding device is moved toward the closed position, and wherein the guide system comprises a movable bearing for the at least partly open holding device.

* * * * *

UNITED STATES PATENT AND TRADEMARK OFFICE
CERTIFICATE OF CORRECTION

PATENT NO. : 6,964,565 B2 Page 1 of 1
APPLICATION NO. : 10/782487
DATED : November 15, 2005
INVENTOR(S) : Abels et al.

It is certified that error appears in the above-identified patent and that said Letters Patent is hereby corrected as shown below:

Column 2,
Line 66, before "arranged" delete "be".

Column 5,
Line 32, before "the completely" insert -- in --.

Column 7,
Lines 35 and 42, after "FIG. 7B" change "show" to -- shows --.
Line 66, after "the joint" delete "or".

Signed and Sealed this

Twenty-seventh Day of June, 2006

JON W. DUDAS
*Director of the United States Patent and Trademark Office*